United States Patent [19]

Villarejos et al.

[11] Patent Number: 4,702,909
[45] Date of Patent: Oct. 27, 1987

[54] NON-A, NON-B HEPATITIS ANTIGEN, ANTIGEN COMPOSITIONS, VACCINE AND DIAGNOSTIC REAGENT

[75] Inventors: Victor M. Villarejos; Kirsten A. Visona, both of San Jore, Costa Rica

[73] Assignee: Louisiana State University A & M, Baton Rouge, La.

[21] Appl. No.: 604,061

[22] Filed: Apr. 26, 1984

Related U.S. Application Data

[63] Continuation-in-part of Ser. No. 374,846, May 5, 1982, abandoned.

[51] Int. Cl.$^4$ .................. A61K 39/12; G21N 33/531; C12N 7/00; C12N 7/02
[52] U.S. Cl. ...................................... 424/89; 436/543; 436/820; 436/5; 435/235; 435/239
[58] Field of Search ............... 424/89, 86; 435/5, 235, 435/239; 436/515, 518, 524, 536, 820; 260/112 R; 530/387, 806, 826

[56] References Cited

U.S. PATENT DOCUMENTS

| | | | |
|---|---|---|---|
| 4,291,020 | 9/1981 | Tabor et al. | 424/89 |
| 4,395,395 | 7/1983 | Tabor et al. | 424/89 |
| 4,464,474 | 8/1984 | Coursaget et al. | 436/820 X |
| 4,511,556 | 4/1985 | Purcell et al. | 514/743 |
| 4,542,016 | 9/1985 | Trepo | 424/86 |

FOREIGN PATENT DOCUMENTS

| | | | |
|---|---|---|---|
| 0061974 | 10/1982 | European Pat. Off. | 424/89 |
| 0093430 | 11/1983 | European Pat. Off. | 424/89 |
| 55-122156 | 9/1980 | Japan | 436/820 |
| 57-175127 | 10/1982 | Japan | 424/89 |
| W082/00205 | 1/1982 | PCT Int'l Appl. | 424/89 |
| WO83/04371 | 12/1983 | PCT Int'l Appl. | 424/89 |

OTHER PUBLICATIONS

Alberti, A., Realdi, G., Bortolotti, F., Busachi, C. A., and Badiali, L., presented at the Int. Symp., Non-A, Non-B, Hepatitis, Vienna, Jun. 16-18, 1980.
Alter, H. J., Holland, P. V., Morrow, A. G., Purcell, R. H., Feinstone, S. M., Moritsugu, Y. Lancet 2: 838-841, 1975.
Alter, H. J., Holland, P. V., and Purcell, R. H., Amer. J. Med. Sci., 270: 392-334, 1975.
Arnold, W., Reiter, H. J., Martini, C. A., and Meyer zum Büschenfelde, K. H., Gastroenterology, 79: 1098, 1980.
Avrameas, S., Immunochemistry 6: 43-52, 1969.
Blumberg, B. S., Bull. N. Y. Acad. Med. 40: 377, 1964.
Bradley, D. W., Cook, H. E., Maynard, J. E., McCaustland, K. A., Ebert, J. W., Dolana, G. H., Petzel, R. A., Kantor, R. J., Heilbrum, A., Fields, H. A., and Murphy, B. L., J. Med. Virol. 3: 253-269, 1979.
Coursaget, P., Maupas, P., Levin, P., and Barin, F. Lancet 2: 92, 1979.
Dienstag, J. L., Bhan, A. K., Alter, H. J., Feinstone, S. M., and Purcell, R. H., Lancet 1: 1265-1267, 1979.
Diermietzel, R., Scheirmann, N., Kuwert, E. K., and Goebell, H., presented at the Int. Symp. Non-A, Non-B Hepatitis, Vienna, Jun. 16-18, 1980.
Duermeyer, W., University of California Symposium on Viral Hepatitis, San Francisco, Mar. 8-10, Grune & Stratton, New York, 1984 (in press).
Duermeyer, W., Hellings, J. A., and Stute, R. J. Virol. Methods. 6: 225-232, 1983.
Duermeyer, W., Stute, R., and Hellings, J. A., J. Med. Virol. 11: 11-12, 1983.
Duermeyer, W., Van Der Veen, J., Koster, B., Lancet 1: 823-824, 1978.
Feinstone, S. M., Kapikian, A., and Purcell, R. H., Science 182: 1026, 1973.
Gerety, R. J., Non-A, Non-B Hepatitis, Academic Press Inc., N.Y., 1981.
Gibo, Y., Akahane, A., Koike, Y., Kiyosawa, K., Nagata, A., and Furuta, S., Lancet Hepatogastroenterology Int. Congr. Gastroenterol., 11th, 1980, p. 355.
Haste, G., Vitvitski, L., and Trepo, C. J., Med. Virol. 5: 73-86, 1980.
Hoffnagle, J. H., J. Med. Virol. 7: 315-319, 1981.
Mori, Y., Ogata, S., Ata, S., and Nakano, Y., Lancet 2: 318, 1980.
Ohori, H., Kanno, A., Nagastsuka, Y., Yamada, E., Onodera, Sh., Tateda, A., Abe, Y., Togoh, T., Ishida, N., J. Med. Virol. 12: 161-178, 1983.
Overby, L., Chairez, R., Ling, C. W., and Gitnik, G. L., presented at the Int. Symp. Non-A, Non-B Hepatitis, Vienna, Jun. 16-18, 1980.
Penner, E., Knöflach, P., and Grabner, G., presented at the Int. Symp. Non-A, Non-B Hepatitis, Vienna, Jun. 16-18, 1980.
Poralla, A., Hütteroth, T. H., Arnold, W., Dienes, H. P., Meyer zum Büschenfelde, K. H., Digestion 28: 90-95, 1983.
Prince, A. M., Brotman, B., van der Ende, M. C., Richardson, L., and Kellner, A., Viral Hepatitis, G. N., Vyas ed., The Franklin Institute Press, pp. 633-640, 1978.

(List continued on next page.)

Primary Examiner—Esther M. Kepplinger
Assistant Examiner—Shawn P. Foley
Attorney, Agent, or Firm—Llewellyn A. Proctor

[57] ABSTRACT

Non-A, non-B hepatitis antigen, antigen compositions, vaccine and assay test for the detection of non-A, non-B hepatitis antigen. The antigen is characterized as having a particle size of about 2.0 nm to about 5.0 nm, a density of from about 1.24 to about 1.30 g/cm$^3$, contains ribonucleic acid and occurs either free or bound to IgG molecules.

The antigen can be isolated by isopycnic banding and chromatographic fractionation, and preferably by enzymatic digestion, isopycnic banding and chromatographic fractionation.

15 Claims, No Drawings

OTHER PUBLICATIONS

Prince, A. M., Trepo, C., Vitvitski, L., Brotman, B., Richardson, L., Huang, C. Y., van den Ende, M. C., and Hantz, O., presented at the Int. Symp. Non-A, Non-B, Hepatitis, Vienna, Jun. 16–18, 1980.

Renger, V. F., Frank, K. H., Porst, H., and Hinkel, K., presented at the Int. Symp. Non-A, Non-B Hepatitis, Vienna, Jun. 16–18, 1980.

Roggendorf, M., and Deinhardt, F., Viral Hepatitis, L. R. Overby, F. Deinhardt and J. Deinhardt, Eds. Marcel Dekhey, New York, pp. 125–131, 1983.

Shirachi, R., Shiraichi, H., Tateda, A., Kikuchi, K., and Ishida, N., Lancet 2: 853–856, 1978.

Storch, E., and Hagert, M., presented at the Int. Symp. Non-A, Non-B Hepatitis, Vienna, Jun. 16–18, 1980.

Suh, D. J., White, Y., Eddleston, A. L. W. F., Amini, S., Tsiquaye, K., Suckerman, A. J., and Williams, R., Lancet 1: 178–180, 1981.

Tabor, E., Mitchell, F. D., Coudeau, A. M., and Gerety, R. J., Med. Virol. 4: 161–169, 1979.

Trepo, C., Vitvitski, O., Hantz, C., Pichoud, C., Grimaud, J. A., Blanchy, B., and Stepetjan, M., presented at the Int. Symp. Non-A, Non-B Hepatitis, Vienna, Jun. 16–18, 1980.

Zhuang, Hui, Coulepis, A. G., Locarnini, S. A., Kaldor, J., Marshall, J. A., and Gust, I., J. Med. Virol. 11: 267–276, 1983.

Vitvistski, L., Trepo, C., Prince, A. M., and Brotman, B., Lancet 2: 1263–1267, 1979.

Voller, A., Bidwell, D. E., and Bartlet, A., Bull. Wld. Hlth. Org. 53: 55–56, 1976.

Yoshizawa, H., Akahane, Y., Itoh, Y., Iwakiri, S., Kitajima, K., Morita, M., Tanaka, A., Nijiri, T., Shimizu, M., Miyakawa, Y., and Mayumi, M., Gastroenterology 79: 512–520, 1980.

NON-A, NON-B HEPATITIS ANTIGEN, ANTIGEN COMPOSITIONS, VACCINE AND DIAGNOSTIC REAGENT

ACKNOWLEDGMENT

The invention described herein was made in the course of or under a grant from the United States Government.

RELATED APPLICATION

This is a Continuation-in-part of Application Ser. No. 374,846 filed May 5, 1982, now abandoned. The subject matter of this Application, herein referred to, is totally incorporated by way of reference and made part of this Application.

FIELD OF THE INVENTION

This invention relates to a purified non-A, non-B hepatitis antigen, compositions of the antigen with other substances, a vaccine, and assay test for the detection of the non-A, non-B hepatitis antigen.

The non-A, non-B Hepatitis Antigen described herein has been deposited with the American Type Culture Collection (ATCC) at 12301 Parklawn Drive, Rockville, Md. 20852 U.S.A under ATCC designation No. 40322. (1) The deposit will be maintained for a period of thirty years, for five years after the last request for the antigen, or for the enforceable life of the U.S. Patent, whichever is longer. (2) Should the deposit become non-viable it will be replaced by Applicants. (3) Assurance of access to the deposit as determined by the Commissioner under 37 CFR 1.14 is provided for. (4) All restrictions on the availability of the deposit to the public will be irrevocably removed upon the granting of a patent.

BACKGROUND AND PRIOR ART

Since the discovery of hepatitis B surface antigen (HBsAg) by Blumberg, Bull. N.Y. Acad. Med. 1964, 40, 7 and of hepatitis A virus (HAV) Feinstone et al., Science, 73, 182, 1026, hepatitis types A and B have become distinguishable by specific serological tests. A further type of hepatitis, in which no agent has yet been identified, has been designated "non-A, non-B (NANB) hepatitis". In the United States of America, where HBsAg-positive donor blood now is excluded from use in transfusions, non-A, non-B hepatitis accounts for approximately 89% of cases of post-transfusion hepatitis, Alter et al., Lancet 2:838–841, 1975, Alter et al., Am. J. Med. Sci., 270:329–334, 1975. Between 5.4 and 18.5% of Americans receiving five units or less of transfused blood develop non-A, non-B hepatitis, Alter et al., op. cit. Although the name "hepatitis C" has been proposed for this disease, most clinicians and investigators have continued to refer to it as non-A, non-B hepatitis because circumstantial evidence suggests that more than one agent may transmit this disease. The diagnosis of non-A, non-B hepatitis is still based on the exclusion by serologic tests of known etiologic agents: HAV and hepatitis B virus (HBV), cytomegalovirus, Epstein-Barr virus, varicella-zoster, or herpes simplex and of Toxic and drug related hepatitis.

In spite of all efforts, the etiologic agent(s) of non-A, non-B hepatitis is still unknown and there is no serologic test available for diagnosis of the disease or identification of chronic carriers.

A variety of particles supposedly associated with non-A, non-B hepatitis have been found in the serum of humans or chimpanzees, having widely different morphology, and ranging in size from 20–27 nm (Gibo et al., 1980; 25–30 nm (Bradley et al., 1979; Yoshisawa et al., 1980; Mori et al., 1980); 36.5 and 61 nm (Diermietzel et al., 1980); 35–40 nm (Hantz et al., 1980) to 60–80 nm (Prince et al., 1978). In 1979 Coursaget et al., described 60 nm particles resembling toga-virus, found in urine and some times in serum of non-A, non-B hepatitis. None of these particles have been shown to be consistently associated with the illness; therefore, it has been concluded that the specific agent of non-A, non-B hepatitis has not yet been discovered.

Similarly various antigen-antibody systems supposedly associated with non-A, non-B hepatitis have been reported in the literature. The first non-A, non-B antigen-antibody precipitin reaction was purportedly found by Schirachi et al., in 1978. However, this was shown to be non-specific (Suh et al., 1982), as were antigen-antibody systems for non-A, non-B hepatitis, detected later such as those reported by Tabor et al., (1979); Vitvitski et al., (1979); Overby et al., (1980); Renger et al., (1980); Arnold et al., (1980); Prince et al., (1980); Trepo et al., (1980); Alberti et al., (1980). The specificity of any of these antigen-antibody reactions for non-A, non-B hepatitis has not been demonstrated and most of them have been shown to detect non-specific immune complexes rather than specific viral components (Suh et al., 1981; Hoofnagle, 1981) or abnormal lipoproteins produced as a result of acute liver damage in non-A, non-B and other forms of viral hepatitis (Hui et al., 1983).

Immune complexes have been demonstrated in cases of non-A, non-B hepatitis by Dienstag et al. (1979); Storch and Hagert (1980) and Pennert et al. (1980), but no specific non-A, non-B antigenic component could be identified. More recently, Poralla et al. (1983) failed to identify the antigen described as non-A, non-B specific by Arnold (1980) in circulating immune complexes in the serum of non-A, non-B hepatitis patients. Also, rheumatoid factor-like reactions may interfere in assays designed to detect non-A, non-B hepatitis antigens, leading to false positive results (Roggendorf and Deinhardt, 1983; Duermeyer, 1984).

This subject has been reviewed by R. J. Gerety (Non-A, Non-B Hepatitis, Academic Press, 1981, Chapter 13, pp 207–228), who concludes that neither viral particles nor antigens specific for non-A, non-B hepatitis have yet been positively identified.

In summary, it is apparent that no specific relationship to non-A, non-B hepatitis infection can be claimed for the diverse particles and antigens found up until now. The agent, or agents which causes non-A, non-B hepatitis remains, until now, unknown; and, until now, there has been no discovery of a true and specific antigen for non-A, non-B hepatitis.

OBJECTS OF THE INVENTION

It is nonetheless among the objectives of this invention to provide:

A method for the isolation of non-A, non-B hepatitis antigen;

A method for the detection of non-A, non-B antigen;

Non-A, non-B hepatitis antigen which has immunogenic efficacy and may be used as a vaccine against non-A, non-B hepatitis;

A composition containing non-A, non-B hepatitis which has utility as a diagnostic agent. These and other objects of the invention will be apparent from the following description of the invention.

SUMMARY OF THE INVENTION

Non-A, non-B hepatitis antigen having a particle size of from about 2.0 to about 5.0 nm, density of from about 1.24 to about 1.30 g/cc in CsCl, sedimentation coefficient of from about 30 S to about 40 S (linear sucrose gradient), and it contains ribonucleic acid. The antigen can be further characterized as being stable overnight to heat at 60° C., but at 70° C. is inactivated after one hour. At pH of 3 and 11, respectively, the antigen is inactivated after one hour, but is stable at pH of about 4-10. The antigen is stable in ether (dimethyl ether).

The non-A, non-B hepatitis antigen in purified form can be isolated from the serum of patients infected with non-A, non-B hepatitis by isopynic banding and chromatographic fractionation, and preferably by enzymatic digestion of the serum, followed by isopynic banding and chromatographic fractionation.

In *J. Infect. Dis. Vol.* 147:702-710 (April 1983) in an article titled "Evaluation of the Specificity of an Immunoprecipitin Test for Non-A, Non-B Hepatitis", herewith fully incorporated by reference, Applicants report the finding of a precipitin reaction, designated the "ICMRT system", specifically associated with non-A, non-B hepatitis. The stability of this reaction under widely different conditions of substrate, pH and type of buffer, and its evident specificity, indicated that the lines of precipitation were true antigen-antibody reactions between specific corresponding entities, that is, a specific non-A, non-B antigen and its homologous antibody, as contrasted, e.g., with the previously reported non-specific precipitin reactions characterized by Suh et al. (1981), supra.

The results of clinical and epidemiological investigations have fully supported the serological evidence of a true association of the ICMRT antigen with non-A, non-B hepatitis.

The precipitating ICMRT antigen has been isolated and purified, and a sensitive enzyme-linked assay (ELISA) and an immune adherence hemagglutination test (IAHA) has been devised for the detection of the antigen and homologous antibodies.

DETAILED DESCRIPTION OF THE INVENTION

According to the present invention a sample of blood from a patient clinically diagnosed as having non-A, non-B diagnosis by (1) elevated liver enzymes determined by specific assays used in diagnosing liver disease, (2) possible clinical symptoms including jaundice, and (3) absence of HAV or HBV current active infection as determined by diagnostic assays is converted into serum by standard methods. The serum is then used to screen sera from blood donors to locate serum containing non-A, non-B antibody. An immunodiffusion assay is used to determine the presence of antibody in a specific serum sample.

Once serum containing non-A, non-B antigen is identified, the serum is subjected to isopycnic banding and fractions of the density gradient are assayed for antigenic activity using the immunoadherence assay test, or immunodiffusion test, or both. In a preferred method the serum is subjected to enzymatic digestion, and the digested serum then subjected to isopycnic banding and chromatographic fractionation.

Enzymatic digestion is employed for the isolation and purification of the antigen with an enzyme which will break down and destroy serum proteins by digestion, but which will not attack the antigen. Tests have shown that the antigen is resistant to attack by certain enzymes, e.g. Trypsin (Bovin pancreas, Sigma T-8253), Papain (Sigma P-3125), Proteinase K (Merck), Proteinase from *Tritirachium Albus* (Sigma P-0390), but yet these enzymes will attack, break down and destroy serum proteins.

The enzymatic digestion, or isolation and purification procedure, consists in first diluting an antigen positive sera and incubating it with the enzyme, to which is added a buffer sufficient to maintain a near neutral pH. Suitably, a 1:2 dilution of the antigen positive sera in pBS buffer at pH 7.4 is employed, along with 1.0 mg per ml of purified Trypsin and 1 mmol $Mg^{++}$ cofactor to activate the enzyme. The mixture is incubated at 37° C. for about 3 hours, after which time the digestion was stopped by the addition of an enzyme inactivator. Thereafter, the broth was centrifuged, e.g. for 10 minutes at 2000 rpm, to separate debris or solids material from the sera.

Successful enzymatic digestion of such sera has also been achieved using other proteolytic enzymes, e.g. 0.5 mg/ml Chymotrypsin (Sigma T-8253), 0.2 mg/ml Papain (Sigma P-3125), 0.3 mg/ml Proteinase K (Merck), and 0.3 mg/ml Proteinase from *Tritirachium Albus* (Sigma P-0390). Trypsin inhibitor was used as the enzyme inactivator, at twice the concentration of trypsin and chymotrypsin; and phenyl-methylsulfanyl fluoride (PMSF) was used for the same purpose with the other enzymes at the indicated concentrations. None of these procedures adversely affected the antigen, which withstood proteolysis at the concentrations stated. After the enzymatic digestion the sera can be subjected to isopycnic banding and fractions containing the antigens identified by examination with the immunoadherence assay method, or immuno diffusion test, or both.

The density gradient may be, e.g. CsCl, NaBr, or sucrose. In the case of CsCl the non-A, non-B hepatitis antigen is found in the region having a density of from about 1.24 to about 1.30 g/cc. This antigen has a particle size of from about 2 to about 5 nm and is stable between pH 4 and pH 10. This antigen may be a subunit component of large viral-like particles of up to about 40 nm which have been observed in higher density regions of from about 1.31 to about 1.34 g/cc.

The density gradient fractions having antigenic activity are pooled and placed on a chromatographic column. Fractions from the column are analyzed using the immunoadherence assay using previously described antibody, and fractions showing presence of antigen are collected. Antigenicity is found in those fractions having a molecular weight of from about 200,000 to about 300,000 daltons. Some antigenicity is also found in the higher molecular weight fractions ranging in molecular weight from about 800,000 to about 1,000,000 daltons. The higher molecular weight fractions are constituted of non-A, non-B hepatitis antigen complexed with lipoproteins of host origin (human), and immunoglobin G, IgG. The true molecular weight of the antigen thus ranges from about 200,000 to about 300,000 daltons, but when complexed with lipoproteins and/or IgG the higher molecular weight complex can also show antigenic properties. Sodium dodecyl sulfate treated antigen shows a component having a molecular weight of about 50,000 daltons using the western block method, Tobin et al., J. Proc. Nat. Acad. Sci. Vol. 76, p. 4350 (1979).

The fractions may be dialyzed if the antigen is desired in a solvent other than that used to elute the column.

The antigen may be inactivated for vaccine use by treatment with formalin at a concentration of from about 1:1,000 to about 1:10,000 for from about 24 to about 120 hours, at any temperature. Preferred conditions are a formalin concentration of about 1:4,000 for about 72 hours at a temperature of from about 33 to about 41° C.

The antigen optionally may be adsorbed on alum to increase its immunogenicity and optionally may be administered in conjunction with other adjuvants.

The non-A, non-B hepatitis antigen of the present invention is immunogenic to susceptible species, e.g., chimpanzees and humans, at a dosage level of from about 1 to about 100 ug, preferably from about 5 to about 50 ug, and most preferably from about 10 to about 30 ug.

ELISA Test For NANB Antigen

An enzyme-linked immunosorbent assay (ELISA) for detection of the non-A, non-B hepatitis antigen has been developed. This test, termed an ELISA sandwich test with alkaline phosphatase tagging is employed to detect the presence of the non-A, non-B antigen in blood sera from non-A, non-B hepatitis cases, and chronic carriers.

(a) To obtain the antibody moiety used in this test, the antibody-containing globulins of anti non-A, non-B (NANB) hepatitis positive sera gamma M globulin, IgM, and gamma G globulin, IgG, fractions were separated in a G-200 Sephadex column calibrated with PBS or a Sephacryl, 300 column calibrated with Tris buffer. The eluted IgM and IgG fractions were further purified by electrophoresis in a $4'' \times 3\frac{1}{4}$ glass plate of 0.85% Gel Agarose for 2 hours at 50V with 25–30 mA. The part of the gel showing M-globulin or G-globulin precipitation was cut out, homogenized in PBS and left overnight at room temperature. After centrifugation the supernatant containing the two or G and M anti-NANB can be used as the antibody moiety for the ELISA test.

(b) Alternatively, the antibody moiety for the ELISA test can be obtained as follows:

An alternate IgG was separated by passing the serum through a Sepharose Protein A column and eluting the IgG fraction with pH 2.8 glycine buffer. The IgM fraction was separated by mixing the serum with Sepharose coupled with Protamine at low ion strength (0.01M) for 12 hours at room temperature and loading a column with this mixture, washing with the same low ion strength phosphate buffer and finally eluting the IgM with 0.08M phosphate buffer.

Preferably the antibody used for detection of the antigen is the IgM fraction of the non-A, non-B hepatitis antibody.

On conducting the ELISA test, the bottom of a test tube is first coated with an antibody-containing globulin of anti non-A, non-B hepatitis positive sera. The tube is washed out to remove material which does not adhere to the tube wall. Next, the sera suspected of containing the non-A, non-B hepatitis antigen is placed on top of the antibodycontaining globulin, and the tube again washed. The sandwich is formed by next adding more of the antibody-containing globulin, conjugated with alkaline phosphatase forming in effect a "double antibody sandwich". The development of a yellow color on addition of the substrate would indicate a positive test. Conversely, the failure to develop a yellow color would indicate a negative test.

The ELISA procedure is more precisely defined as follows:

Each well in the micro-ELISA plates (flat bottom, polystyrene, 96 wells, Dynatech 1-223-29) was coated with 0.2 ml of an antibody solution adjusted to contain 10 ug/ml protein in carbonate buffer at pH 9.6. The plates were kept for 24 hours at 5° C. and post-coated for 8 hours at 5° C. with a solution of 2% Polyvinyl Pyrrolidone (PVP 40,000) and 0.1% bovine albumin in the same carbonate buffer.

To each precoated well 0.1 ml of patient serum and 0.1 ml of PBS containing 4% bovine albumin and 0.5% Tween 20 were added. The plate was incubated at 37° C. (waterbath) for 1 hour, and then washed three times with PBS containing 0.5% Tween 20.

To each well, 0.2 ml of anti-NANB gamma-globulin G or M (protein concentration of about 2 ug/ml) conjugated with alkaline phosphatase by the glutaraldehyde method (Avrameas, 1976) was added and again incubated at 37° C. for 1½hour. After washing three times as before, 0.2 ml of 1 gm/ml p-nitrophenil phosphate in diethanilamine buffer pH 9.8 was added as substrate and incubated at 37° C. for 2 hours. Results were read on a Micro-ELISA Auto Reader (Dynatech), at 405 nm wave length.

Samples with a P/N ratio 2.5 were considered presumptively positive for antigen and were confirmed by a blocking test with sera positive and negative for non-A, non-B hepatitis antibodies.

ELISA Test For NANB Antibody

The same test, slightly modified with an inhibition step, can be used to detect the non-A, non-B hepatitis antibody.

The preparation procedure of the antibody containing serum used for coating the micro-plate and of the gamma-globulin conjugate is the same as used for the antigen assay. The antigen used in this assay is the antigen purified by enzymatic digestion and CsCl gradient and chromatographic fractionation, having an identity of 1.24 to 1.30 grams/cm$^3$. The fractions corresponding to these densities are dialized against PBS, pooled and digested by the method used for purification of the antigen, and adjusted to an absorbance of approximately 1.0 at 405 nm when testing negative sera. Equal amounts of adjusted antigen solution and serum sample were mixed and incubated for 1 hour at 37° C., and 0.1 ml of this mixture was added to each antibody coated well of a micro-plate together with 0.1 ml of PBS buffer with bovine albumin and Tween 20. Afterwards the same procedure was followed as for detection of the antigen. Samples with an inhibition of 50% 8c or above were regarded as possible.

The following non-limiting examples are further illustrative of the invention.

EXAMPLE 1

Isolation of Non-A, Non-B Hepatitis Antigen

An individual having clinical symptoms of hepatitis disease as determined by elevated levels of serum glutamic oxaloacetic transaminase and serum glutamic pyruvate transaminase enzymes, presence of jaundice, and who was determined not to be suffering from either HAV or HBV by radio-immune diagnostic assays, was bled and the blood converted into serum by known methods. Samples of this serum were used to screen various samples of serum until a serum containing antibody as determined by the immunodiffusion assay (Abbott rheophoresis plate) was located.

The serum, 7 ml, containing the non-A, non-B antigen was placed on a 31 ml CsCl density gradient made up of five 6.2 ml quantities of the following densities of CsCl: 1.1, 1.2, 1.3, 1.4, and 1.6. The density gradient with the serum sample on top was placed in a Beckman SW27 rotor and spun at 25,000 rpm for 16 hours. One ml fractions were taken and dialyzed against water. The fractions were then lyophilized and reconstituted to 200 ul with distilled water. The fractions were then assayed for antigenic activity in the immune adherence assay (and/or immune diffusion test) using the previously described antibody. Activity was found at a density between 1.24 and 1.30 g/cc with a maximum at 1.27.

A 10 ml Sepharose CL6B column having a length of approximately 25 cm and a diameter of approximately 7 mm was packed by conventional methods. A charge, 0.4 ml, of pooled density gradient fractions that had been dialyzed and reconstituted as described in the preceding paragraph were placed on the column. The column was eluted with phosphate buffered saline (PBS) at approximately 1 ml per 15 minutes and 0.5 ml fractions were collected. These fractions were then lyophilized and reconstituted in distilled water at 100 ul per fraction. The fractions were then analyzed in the immune adherence assay (and/or immuno diffusion test) using the previously isolated antibody. The maximum antigenic activity corresponded to those fractions having a molecular weight of approximately 200,000 to 300,000 daltons, with another peak of activity ranging from about 800,000 to 1,000,000 daltons. This latter peak is due to the presence of the antigen complexed with host lipoproteins.

EXAMPLE 2

Preparation of Non-A, Non-B Hepatitis Vaccine

The material eluted from the Sepharose CL6B column in Example 1 having a molecular weight ranging from 200,000 to 300,000 daltons is pooled and mixed with formalin at a concentration of 1:4,000 for 72 hours at 37° C. to inactivate the antigen and provide a material suitable for use as a vaccine.

EXAMPLE 3

Preparation of Alum-Adsorbed Vaccine

The inactivated product of Example 2 is adsorbed on alum and suspended in physiological saline solution buffered at from pH 6.0 to 7.8.

EXAMPLE 4

The fractions eluted from the Sepharose CL-6B in Example 1 showing antigenic activity are dialyzed against distilled water to provide the non-A, non-B antigen in a composition comprising distilled water.

This composition is useful either as a vaccine after inactivation as described in Example 2 or as such or as a diagnostic antigen.

EXAMPLE 5

The fractions eluted from the Sepharose CL-6B column in Example 1 which show antigenic activity are dialyzed against saline to provide the non-A, non-B antigen in a composition comprising saline. This composition is useful either as a vaccine after inactivation as described in Example 2 or as such or as a diagnostic antigen.

EXAMPLE 6

Approximately 10 mg of non-A, non-B hepatitis antigen from the Sepharose CL-6B column was mixed with 2% sodium dodecyl sulfate and 5% 2-mercaptoethanol solution in 5 ml of tris buffer adjusted to pH 6.8 with concentrated HCl. The solution was incubated at 100° C. for 3 minutes and 0.5 ml of 50% glycerol and 0.5% bromophenol blue tracking dye were added to the solution. The preparation was applied to a 450 $cm^3$ column of 12.5% polyacrylamide gel with a 5% stacking gel over it. The gel column was developed with 1.5 liters of tris-glycine-sodium dodecyl sulfate buffer in an electric field of 100 volts. Development was continued for 15 hours. A p50,000 daltons molecular weight band was located in the gel by comparison with a coomassie blue stained track run in parallel. The region was cut from the gel and eluted with 20 ml of physiological saline/0.1% sodium dodecyl sulfate solution. The sodium dodecyl sufate solution was removed by extensive dialysis against physiological saline and was ready for formulation into a vaccine.

EXAMPLE 7

Preparation of Non-A, Non-B Hepatitis Vaccine

The material eluted from the Sepharose CL6B column in Example 1 having a molecular weight ranging from 200,000 to 300,000 daltons is pooled and then subjected to enzymatic digestion. An antigen positive sera is buffered with PBS in dilution ratio of 1:2, 1.0 mg per ml of purified Trypsin added, 1 mmol of $Mg++$ added as cofactor, and the mixture incubated at 37° C. for 3 hours. The enzyme is their inactivated by addition of Trypsin inhibitor. The solution was then treated with formalin at a concentration of 1:4,000 for 72 hours at 37° C. to inactivate the antigen and provide a material suitable for use as a vaccine.

The immune adherence assay used herein for detection of the non-A, non-B hepatitis antigen or antibodies is based on the method described by Mayumi et al (Vox Sang. 20; 178, 1971) for detection of hepatitis B antigen (HBsAg).

Reagents

Reference sera positive for ICMRT antigen or antibody were used for the test. Antigen positive sera were cross titrated with antibody positive sera to establish the endpoint or immune adherence unit.

The use level for both antigen and antibody determinations was 4 to 8 IA titration units.

For complement fesh guinea pig serum is used at 1:50 to 1:100 dilution.

A 0.5% suspension of human red blood cells from selected donors (type O - Rh-) are prepared daily from citrated whole blood kept refrigerated for 2 -4 weeks.

U - shaped polysterene microplates, 96 wells, are used.

The assay

The two sera are heated for 45 minutes at 56° C. to inactivate complement.

When titrating for antigen:

1. 0.05 ml of heated sample is placed in well #1 of duplicate lines and serially diluted out, using 0.025 ml blanks of gelatin veronal buffer, GVB.

2. A known antibody positive serum is added at the appropriate dilution (4–8 IA units) to one line and GVB is added to the duplicate line as a control. The plate is mixed on a vibrating mixer (10 seconds) and incubated at 37° C. for 1 hour.

3. Complement at appropriate dilutions is added (1:50 to 1:100) to all wells (0.025 ml). The plates are again mixed for 10 seconds and incubated at 37° C. for 40 minutes.

4. The micro-plates are removed from incubator and 0.025 ml of DDT (Dithiotrietol) is added to all wells. The plates are again mixed.

5. Immediately 0.025 ml of 0.5% RBC is added to all wells and, after mixing, the plates are left at room temperature for at least 2 hours for a pattern of agglutination to develop. Since the process is not reversible, overnight settling is sometimes practical. A lid or cover is used on the plates throughout so as to avoid evaporation of sample.

Each run has a control antigen and antibody assayed and titer of each reported.

6. When titrating for antibody:

0.05 ml of sample is placed in well #1 of duplicate lines and serially diluted out, using 0.025 ml blanks of GVB and tulip automatic or manual diluters.

7. Hepatitis antigen at appropriate dilution is added to line 1. (Use level is 4 to 8 units.) GVB is added ro duplicate line as a control. Plate is mixed (20 seconds on Thomas vetro mixer) and incubated at 37° C. for 1 hour.

8. Remaining procedure is the same as for antigen titrations.

It is apparent that various minor modifications and changes can be made in the procedure, as will be apparent to those skilled in this art; without departing the spirit and scope of the invention.

Having described the invention what is claimed is:

1. A substantially purified non-A, non-B hepatitis antigen ATCC 40322, consisting essentially of particles having a size from about 2.0 to about 5.0 nm, and a density of from about 1.24 to about 1.30 g/cc in CsCl.

2. The antigen according to claim 1 having a molecular weight of from about 200,000 daltons to about 300,000 daltons.

3. The antigen according to claim 1 which, when complexed with human lipoproteins of host origin, or human, immunoglobin G. has a molecular weight of from about 800,000 daltons to about 1,000,000 ol daltons.

4. A subunit antigenic component of the non-A, non-B hepatitis antigen of claim 1 having a molecular weight of about 50,000 daltons.

5. A composition comprising the antigen of claim 1 in an aqueous vehicle.

6. A composition according to claim 5 wherein the vehicle is water, saline or phosphate buffered saline.

7. The antigen according to claim 1 adsorbed on alum.

8. A vaccine comprising an immunologically effective amount of the antigen of claim 1 and a physiologically acceptable vehicle.

9. The antigen according to claim 1 further defined in that the sedimentation coefficient of the particles ranges from about 30 S to about 40 S (linear sucrose gradient), and it contains ribonucleic acid.

10. A diagnostic reagent comprising the antigen of claim 1 in an aqueous medium in a quantity effective to form an immune complex in a diagnostic assay.

11. A process for isolating a non-A, non-B hepatitis antigen ATCC 40322, subjecting serum containing non-A, non-B hepatitis antigen, ATCC 40322, to isopycnic banding and selecting a fraction having a density equivalent to from about 1.24 to about 1.30 g/cc in CsC1, and a particle size of from about 2.0 to about 5.0 nm.

12. A process according to claim 11 wherein the selected fraction is treated to separate particles having a molecular weight of from about 200,000 to about 300,000 daltons.

13. A process according to claim 11 wherein the selected fraction is treated to separate particles which, when complexed with human lipoproteins of host origin, or human immunoglobin G, have has a molecular weight of from about 800,000 daltons to about 1,000,000 daltons.

14. A process according to claim 11 wherein the treatment separates particles having a molecular weight of from about 200,000 to about 300,000 daltons, and particles having a molecular weight of from about 800,000 to about 1,000,000 daltons.

15. The process according to claim 11 wherein the antigen is further defined in that the sedimentation coefficient of the particles ranges from about 30 S to about 40 S (linear sucrose gradient), and contains ribonucleic acid.

* * * * *